United States Patent [19]

Lupo et al.

[11] Patent Number: 5,120,809
[45] Date of Patent: Jun. 9, 1992

[54] AMPHIPHILIC MONOMERS WITH MIXED-CHAIN STRUCTURE AND POLYMERS AND FILM COMPOSED OF AT LEAST ONE MONOMOLECULAR LAYER THEREOF

[75] Inventors: Donald Lupo, Eppstein/Taunus; Werner Prass, Mainz; Ude Scheunemann, Liederbach, all of Fed. Rep. of Germany

[73] Assignee: Hoechst Aktiengesellschaft, Frankfurt am Main, Fed. Rep. of Germany

[21] Appl. No.: 453,669

[22] Filed: Dec. 20, 1989

[30] Foreign Application Priority Data

Dec. 22, 1988 [DE] Fed. Rep. of Germany ....... 3843194

[51] Int. Cl.$^5$ ............ C08F 20/54; C08F 20/58; C08F 20/60
[52] U.S. Cl. ............... 526/306; 526/303.1; 526/304; 526/307.2; 526/310; 526/312; 526/318; 526/320; 526/321; 564/152; 564/169; 564/193; 564/199; 564/204
[58] Field of Search ............... 526/304, 303.1, 306, 526/310, 312; 564/204

[56] References Cited

PUBLICATIONS

Kunitake et al., J. Micromol. Sci., Chem., 1984, A21 (8-9), 1237-52.
Elbert et al., J. Am. Chem. Soc., 1985, 107, 4134-4141.

*Primary Examiner*—Fred Zitomer

[57] ABSTRACT

Amphiphilic monomers with mixed-chain structures of the formula

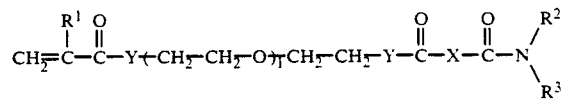

in which
Y denotes —O— or —NH—
X denotes a group of the formula —$(CH_2)_n$— or —$(CH_2-O-CH_2)_n$—
l denotes an integer from 0 to 10,
n denotes an integer from 1 to 10,
$R^1$ denotes hydrogen, methyl, chlorine, cyano, fluorine or bromine,
$R^2$ denotes $C_1$-$C_{24}$-alkyl or $C_1$-$C_{24}$-fluoroalkyl and
$R^3$ denotes $C_8$-$C_{24}$-alkyl or $C_8$-$C_{24}$-fluoralkyl, with the proviso that the groups $R^2$ and $R^3$ contain a different number of carbon atoms. The monomers are polymerized on their own or together with other comonomers. The polymers obtained are suitable for the preparation of ultra-thin layers on a suitable layer support.

9 Claims, No Drawings

AMPHIPHILIC MONOMERS WITH MIXED-CHAIN STRUCTURE AND POLYMERS AND FILM COMPOSED OF AT LEAST ONE MONOMOLECULAR LAYER THEREOF

The invention relates to specific amphiphilic monomers with alkyl side-chains and polymers thereof, to a film composed of at least one monomolecular layer of these molecules on a solid layer support (=so-called layer elements) and a process for the preparation of the monomers, the polymers and the layer elements.

The preparation of ordered layers of organic polymers having long-chain side groups is predominantly carried out using the Langmuir-Blodgett (LB) process. In this process, molecules are spread on an aqueous surface and the long alkyl side groups are arranged parallel by reducing the surface per molecule. Under constant thrust, the molecules are taken up onto a substrate by being dipped and withdrawn. In this process, each dip transfers a monomolecular layer while retaining the order in the layer.

LB films are constructed using amphiphilic molecules, i.e. molecules having a hydrophilic end (a "head") and a hydrophobic end (a "tail"). Greater stability of the LB films has already been achieved by preparing polymeric LB films.

For this purpose, unsaturated amphiphiles have on occasion been polymerized after preparation of the film. However, organic polymers with long alkyl side chains have also already been used directly for layer preparation (WO83/03165 and R. Elbert, A. Laschewsky and H. Ringsdorf, J.Am.Chem.Soc. 107, 4134–4141 (1985)). However, both types of polymeric films have more defects than occur in monomeric films. The polymerization of the layer in almost every case causes a contraction of the layer with the formation of defects. In the case of copolymer films, as described by A. Laschewsky, H. Ringsdorf, G. Schmidt and J. Schneider in J.Am.Chem.Soc. 109, 788–796 (1987) the randomly incorporated hydrophilic comonomer can cause hydrophilic loops of different length leading to inhomogeneities of layer thickness.

Generally, LB layers can only be constructed from homopolymers if the alkyl side chain and the polymerizable unit are separated by a hydrophilic, flexible segment, the "hydrophilic spacer" (R. Elbert, A. Laschewsky and H. Ringsdorf, J.Am.Chem.Soc. 107, 4134–4141 (1985)). However, LB layers of this type, particularly when prepared as relatively thick layers (200–300 monolayers) again and again have defects in the layer structure which are probably caused by a viscosity which is still too high and consequently too low a flexibility in the polymeric LB layer.

The object was therefore to provide monomers whose homopolymers have a high flexibility and can be particularly well transferred to layer supports even at low temperatures.

This object is achieved by the present invention. It is based on the observation that amphiphiles having two alkyl chains of different lengths bring about greatly increased flexibility in monolayers. This is also true for the polymers. The alkyl radicals of different lengths additionally allow the possibility of "interdigitization" of alkyl chains from two adjacent monolayers in the LB film. This results in increased adhesion in the hydrophobic region of the LB film.

The invention relates to amphiphilic monomers having mixed-chain structures, of the formula

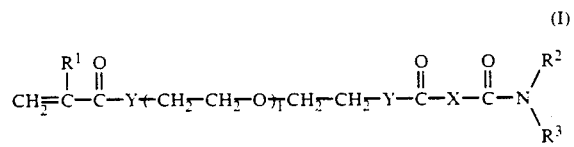

in which
Y denotes —O— or —NH—
X denotes a group of the formula —(CH$_2$)$_n$— or —(CH$_2$—O—CH$_2$)$_n$—
l denotes an integer from 0 to 10,
n denotes an integer from 1 to 10,
R$^1$ denotes hydrogen, methyl, chlorine, cyano, fluorine or bromine,
R$^2$ denotes C$_1$-C$_{24}$-alkyl or C$_1$-C$_{24}$-fluoroalkyl and
R$^3$ denotes C$_8$-C$_{24}$-alkyl or C$_8$-C$_{24}$-fluoroalkyl, with the proviso that the groups R$^2$ and R$^3$ contain a different number of carbon atoms.

Preference is given to alkyl groups in the groups R$^2$ and R$^3$; these may be branched or unbranched. The fluoroalkyl groups may be fully or partially fluorinated, the alkyl group terminating with a trifluoromethyl group for example. In any case, the groups R$^2$ and R$^3$ must be of different lengths.

These monomers of the formula (1) can be prepared by methods known per se in the following manner:

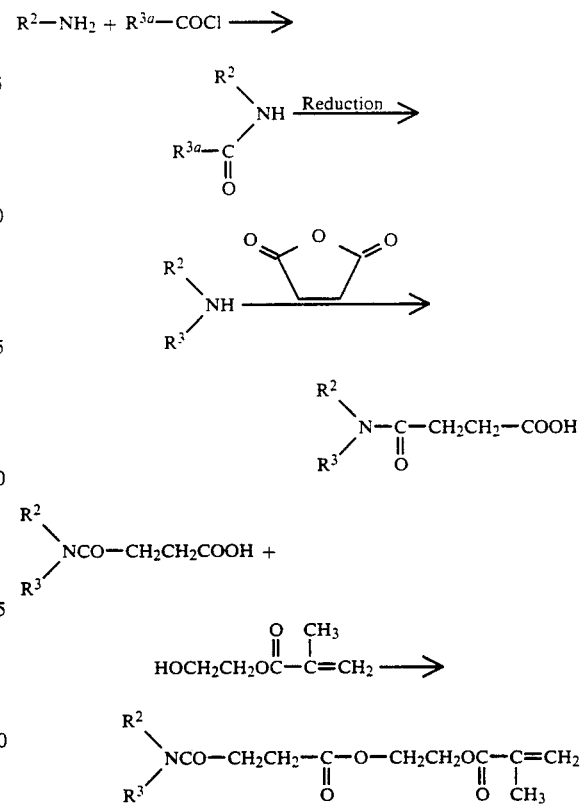

This process is explained in more detail in Example 1 below.

The invention furthermore relates to polymers, preferably in the form of films in at least one monomolecular layer, composed of or containing a monomer of the particular formula I. These polymers may be entirely constructed from the said monomers of the formula I or these novel monomers may also be copolymerized with other, hydrophobic or hydrophilic comonomers. Copolymers of this type preferably contain 1 to 20% by weight of monomer of the formula I and 99 to 80% by weight of a hydrophobic comonomer, or 10 to 99% by weight of monomer of the formula I and 90 to 1% by weight of a hydrophilic comonomer. Furthermore, the polymers may also be constructed from different monomers of the formula I. The preparation of these homopolymers and copolymers is carried out by free-radical initiation using customary processes. The hydrophilic comonomers used are preferably watersoluble vinyl monomers such as, for example, itaconic acid, fumaric acid, maleic acid, acrylic acid, cyanoacrylic acid, and methacrylic acid or the water-soluble derivatives thereof. The derivatives used are in particular the acid amides, acid nitriles and the 2-hydroxyethyl ester.

The hydrophobic copolymer contains, in addition to a polymerizable unit for example a vinyl double bond, at least one alkyl chain having 10 to 24 carbon atoms and/or is soluble in benzene.

The polymers or films according to the invention can also be mixed with other useful components, for example with dyes, amphiphilic crosslinking agents, or monomeric or polymeric amphiphiles.

The proportion of these additives in mixtures of this type may be 10 to 99% by weight.

The preparation of films is carried out by dissolving the polymers according to the invention or mixtures containing these polymers in an essentially volatile water-immiscible solvent and applying (=spreading) them onto the surface of an aqueous solution in a film balance. The average surface per repeating unit is calculated from measuring the surface, the spread volume and the concentration of the solution. Phase transitions which occur when compressing the molecules can be followed from the surface prsssure-area isotherm.

The molecules are thrust together using a barrier, the alkyl chains, with increasing surface density, becoming oriented essentially perpendicular to the boundary layer. During compression, by self-organization of the molecules, a highly ordered monomolecular film is produced at the boundary layer, the constant layer thickness of this film being essentially determined by the chain length of the alkyl side chains of the polymers and their angle of tilt (this is the angle by which the molecular chains on the aqueous surface are inclined towards the normal). The typical thickness of a film of this type is 2-3 nm.

The film is removed from the aqueous surface under constant thrust by dipping in or withdrawing a suitable support with the order being maintained.

The subphase for the preparation of the monofilm is usually water or an aqueous solution. It is however also possible to use other liquids with a high surface tension such as for example glycerol, glycol, dimethyl sulfoxide, dimethylformamide or acetonitrile.

Suitable supports are any desired solid, preferably dimensionally stable substrates made from different materials. The substrates used as layer supports can for example be transparent or light transmitting, electrically conducting or insulating. The substrate can be hydrophobic or hydrophilic. The surface of the substrate to which the LB layer is applied can be rendered hydrophobic. The surface of the substrate which is to be coated should be as clean as possible so that the formation of a thin, ordered layer is not impaired. In particular, the presence of surface-active substances on the surface of the substrates which is to be coated can impair formation of the layer. It is possible initially to provide the substrates used as layer support with an intermediate layer on the surface which is to be coated before applying the LB film in order, for example, to improve the adhesion of the film on the substrate.

Examples of materials which can be used for the substrates are metals such as for example gold, platinum, nickel, palladium, aluminum, chromium, niobium, tantalum, titanium, steel and the like. Other suitable materials for the substrates are plastics, such as for example polyesters, for instance polyethylene terephthalate or polybutylene terephthalate, polyvinyl chloride, polyvinylidene chloride, polytetrafluoroethylene, polystyrene, polyethylene or polypropylene.

Suitable substrates are likewise semiconductors such as silicon, germanium or gallium arsenide or else glass, silicon dioxide, ceramic materials or cellulose products. The surface of glass and other hydrophilic substrates can, if required, be rendered hydrophobic in a manner known per se by reaction with alkylsilanes or hexamethyldisilazane. The selection of substrate materials is governed primarily by the intended use of the layer elements prepared from the film according to the invention. The layer supports used for optical elements are as a rule transparent, light-transmitting substrates. If the layer elements according to the invention are used for example in electronics or in electrochemical processes, the substrates used are in particular electrically conducting materials such as metals or metallic surface layers, for example on plastic films or glass.

The substrates used as supports for the films according to the invention can have any desired forms, depending on the intended use. They may for example be in the form of films, foils, sheets, tapes or cylinders, or other desired forms may be selected. Generally, the layer supports are flat, plane substrates such as for example films, foils, sheets, tapes and the like. The surface of the substrates to be coated is preferably smooth, as is usually the case for preparing LB films. In the case of flat, plane substrates, the films according to the invention can be applied to one or both surfaces of the substrate.

The polymers according to the invention are highly suitable for the preparation of a multilayer structure with few defects, and it is possible to prepare the layer at comparatively low temperatures for polymers and the layer structure is nevertheless still stable even at relatively high temperatures.

Films of this type on substrates are suitable for example for optical waveguide systems or for the preparation of filters for optical purposes. Due to the low critical surface tension, the films are also suitable for improving the frictional properties of materials, for preparating protective layers and also for other relevant applications.

The invention is described in more detail by means of the examples below:

Example 1

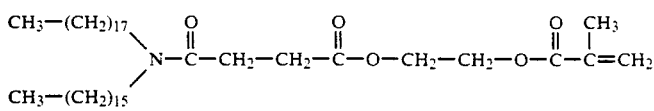

A solution of 27.5 g (0.1 mole) of palmitoyl chloride in 100 ml of dry methylene chloride are added dropwise at 0° C. over a period of 30 minutes to a solution of 26.95 g (0.1 mole) of N-octadecylamine and 12.14 g (0.12 mole) of triethylamine in 500 ml of dry methylene chloride, the mixture is stirred for 2 hours with cooling at 0° C. and then heated to room temperature with stirring. 500 ml of aqueous 1 M HCl solution are then added to the resulting slurry-like material, the mixture is stirred for 30 minutes at room temperature and the product filtered off under suction. The product is then recrystallized from methylene chloride.

20.8 g (82%) of a white powder are obtained having a melting point of 96°-97° C.

$^1$H-NMr (CDCl$_3$, 100 MHz)

$\delta = 0.9$ (t,6H, —CH$_3$); 1.25 (m,58H, —CH$_2$—); 2.0-2.2 (t,2H, —CH$_2$-CO); 3.0-3.3 (m, 2H, N—CH$_2$); 5.2-5.5 (m,1H, —NH)

10 g (0.462 mole) of LiAlH$_4$ are suspended in 100 ml of dry tetrahydrofuran and a suspension of 33 g (65 mmol) of N-octadecylpalmitamide in 500 ml of dry tetrahydrofuran is metered in at room temperature over a period of 20 minutes. After stirring for 30 minutes at room temperature, the mixture is heated and boiled under reflux for 15 hours. After cooling the reaction mixture, the excess of LiAlH$_4$ is destroyed with cooling by careful addition of each 10 ml amounts of water, 15% strength NaOH solution and again water. The resulting aluminum hydroxide is filtered off under suction and washed with toluene. The filtrate is combined with the washings and the solvent removed in vacuo. The product is then recrystallized from ethanol. 26 g (81%) of a white powder are obtained having a melting point of 71.8°-72.6° C.

$^1$H NMR (CDCl$_3$, 100 MHz)

$\delta = 0.9$ (t,6H, —CH$_3$); 1.1-2.05 (m,61H, —CH$_2$—,NH); 2.4-2.7 (t, 4H, N—CH$_2$)

20 g (40.5 mmol) of N-hexadecyl-N-octadecylamine, 8.1 g (81 mmol) of succinic anhydride and 8.2 g (81 mmol) of triethylamine are dissolved in 250 ml of dry toluene and the mixture is boiled under reflux for 2½ days with the exclusion of moisture. After cooling, the reaction mixture is shaken with 1 M HCl and the organic phase is separated off, dried with Na$_2$SO$_4$ and the solvent removed in vacuo. The product is then recrystallized twice from methanol. 22.9 g (95%) of a white powder are obtained having a melting point of 59.8°-60.7° C.

$^1$H NMR (CDCl$_3$, 100 MHz)

$\delta = 0.9$ (t,6H, —CH$_3$); 1.1-1.9 (m,60H, —CH$_2$—); 2.65 (s,4H, CO—CH$_2$—CH$_2$—CO); 3.05-3.45 (m,4H, N-CH$_2$)

4.90 g (8.04 mmol) of N-hexadecyl-N-octadecylsuccinamide, 1.63 g (12.6 mmol) of 2-hydroxyethyl methacrylate and a spatula tip full of 2,6-di-tert-butyl-p-cresol are dissolved in 100 ml of dry methylene chloride and a solution of 1.81 g (8.79 mmol) of dicyclohexylcarbodiimide and 35 mg of freshly recrystallized N,N-dimethylaminopyridine in 20 ml of dry methylene chloride are added dropwise at 0° C. with the exclusion of moisture. At the end of the addition, the mixture is stirred for a further hour at 0° C. Then the reaction mixture is allowed to stand overnight at room temperature and next morning the resulting urea is filtered off under suction. The filtrate is washed twice with 100 ml of water, and dried with Na$_2$SO$_4$ and the solvent is removed in vacuo. After purification by column chromatography (silica gel Si 60, mobile solvent: hexane/ethyl acetate 5:1 (v/v)), 3.93 g (69%) of a white, waxy substance are obtained which melts just above room temperature.

$^1$H NMR (CDCl$_3$, 100 MHz)

$\delta = 0.9$ (t,6H, —CH$_3$); 1.1-1.85 (m,60H, —CH$_2$—); 1.92 (m,3H, C—CH$_3$); 2.65 (t,4H, CO—CH$_2$—CH$_2$—CO); 3.0-3.45 (m,4H, N—CH$_2$); 4.34 (s, 4H, O—CH$_2$—CH$_2$—O); 5.5, 6.1 (AB,2H, C=CH$_2$)

Example 2: Free-radical polymerization of comp. 1

2 g of the monomer prepared in Example 1 are dissolved in 20 ml of tetrahydrofuran and 5.0 mg of azo-bis-isobutyronitrile are added. The solution is introduced into a three-necked flask with reflux condenser (fitted with a gas outlet tube and bubble counter), thermometer and gas inlet tube, and nitrogen is bubbled through the solution for one hour at room temperature. The solution is then heated to reflux (internal temperature: 65° C.) and boiled for eight hours under reflux. During this period, the reaction mixture is constantly stirred by means of a magnetic stirrer and purged with nitrogen. The polymer is precipitated by pouring the reaction solution into 1 l of methanol at $-18°$ C. and filtering off under suction with dry ice cooling. 200 mg of a white, greasy material are obtained which is soft at room temperature, insoluble in hexane and methanol, and soluble in tetrahydrofuran. Molecular weight determination by gel permeation chromatography gave a Mw of 23000 and a Mn of 12000 Dalton (polystyrene calibration).

Example 3: Layer preparation by the Langmuir-Blodgett method

A glass microscope slide (76 mm × 26 mm) is cleaned by the following process: The glass is immersed for one hour in a freshly prepared solution at 60° C. of four parts of conc. H$_2$SO$_4$ and one part of 30% strength H$_2$O$_2$ solution, rinsed with clean water and subjected to ultrasound for 15 minutes at 50° C. in a cleansing solution (Extran/AP 11, concentration: 2-4 g/l). Then the glass is thoroughly rinsed again with clean water and dried in a warm current of air. The glass is then rendered hydrophobic by treatment with hexamethyldisilazane vapor (10 minutes at 70° C.).

Multilayers of the polymer prepared in Example 2 are transferred to the glass slide by the Langmuir and Blodgett process by spreading in a Langmuir film balance 0.25 cm$^3$ of a solution of 5 mg of the polymer in 10 cm$^3$ of a mixture of 1 ml of tetrahydrofuran and 9 ml of CH$_2$Cl$_2$ on an aqueous subphase at a subphase temperature of 10° C. Reduction of the aqueous surface covered by the monofilm is used to set the thrust at 25 mN/m and this value is kept constant. The slide is then dipped vertically from above into the film balance through the aqueous surface (dipping velocity: 20 mm/min) and after a short pause (10 sec.) at the lower reversal point the slide is taken out again (withdrawal velocity: 10 mm/min) a monolayer is transferred to the slide both during the dipping operation and during the withdrawal operation. Multiple repetition of the dipping operation after a pause for 1 minute at the upper reversal point in each case results in a total of 20 double layers being transferred. The transfer rates are 90%. Even when transferring 50 monolayers and above, optically clear, transparent layers are obtained.

Example 4 Ellipsometric measurements of layer thickness and refractive index

A silicon platelet (40 mm×10 mm) is cut from a silicon wafer and cleaned as follows:
1. Treatment for 1 hour in a hot (60° C.), freshly prepared mixture of one part of 30% strength $H_2O_2$ solution and four parts of conc. $H_2SO_4$. The wafer is then rinsed with clean water.
2 Dipping for 30 seconds in HF solution buffered with $NH_4F$ and then rinsing again with clean water.

After this treatment, the silicon platelets are hydrophobic (angle of contact with water: 75°).

Layers of a polymer from monomer 3 are transferred as in Example 3 to the silicon platelet by the Langmuir and Blodgett method (subphase: water at 10° C, thrust: 20 mN/m, dipping velocity: 20 mm/min, withdrawal velocity: 10 mm/min, pause at the upper reversal point: 1 min.). A monolayer is transferred in each case during both dipping and withdrawal (transfer rate: 93%). Samples with in each case 10, 30, 50 and 70 monolayers of the polymer are prepared and the layer thicknesses and the refractive index of the LB films are measured ellipsometrically (result: refractive index at 633 nm: 1.528, layer thickness: 1.66 nm/monolayer).

Example 5: Thermal stability measurements

A silicon platelet (40 mm ×10 mm) is cut from a thermally oxidized silicon wafer (thickness of the oxide layer: 160 nm) and immersed for one hour at 60° C. in a freshly prepared mixture of one part of 30% strength $H_2O_2$ solution and four parts of conc. $H_2SO_4$. After thorough rinsing with clean water, the platelet is treated for 15 minutes at 50° C. in an ultrasound bath with an alkaline cleaning liquor (Extran ® AP 11, concentration 2-4 g/1), thoroughly rinsed with clean water and dried in a current of warm air. The platelet is then rendered hydrophobic by treatment with hexamethyldisilazane vapor (10 minutes at 70° C.).

Coating by the LB method is carried out with 8 monolayers of a polymer of monomer 3, as described in Example 4.

The coated support is heated in a special apparatus with a linear temperature gradient (0.5° C./sec). During the heating operation, the thickness of the LB layer is measured by means of the intensity of a perpendicularly polarized laser beam (633 nm) reflected from the sample. The temperature at which the first change in the layer thickness results is 110° C. with the polymer used (by comparison: with LB layers of 22-tricosoic acid this temperature is 70° C.).

Example 6: Critical surface tension measurements

A silicon platelet (40 mm×10 mm) is cleaned as in Example 4 and as in Example 4 coated with eight monolayers of the polymer from monomer 3 (temperature of the subphase: 10° C.).

Drops of liquid from a range of n-alkanes ($C_{16}H_{34}$—$C_{14}H_{30}$) were introduced to the surface of the transferred layers and the angles of contact of the liquid drops with the surface were measured. These angles of contact allow the critical surface tension to be determined by Zisman's method. A result of 26.5 mN/m is obtained. (By comparison: with a polyethylene surface, this measurement gives a value of 31 mN/m).

| Comp. No. | List of monomers synthesized: Structural formula |
|---|---|
| 1 | $CH_3$—$(CH_2)_{17}$<br>$\phantom{CH_3(CH_2)_{17}}$\N—C(=O)—$CH_2$—$CH_2$—C(=O)—O—$CH_2$—$CH_2$—O—C(=O)—C($CH_3$)=$CH_2$<br>$CH_3$—$(CH_2)_{15}$/ |
| 2 | $CH_3$—$(CH_2)_{17}$<br>\N—C(=O)—$CH_2$—$CH_2$—C(=O)—O—$CH_2$—$CH_2$—O—C(=O)—C($CH_3$)=$CH_2$<br>$CH_3$—$(CH_2)_{13}$/ |
| 3 | $CH_3$—$(CH_2)_{17}$<br>\N—C(=O)—$CH_2$—$CH_2$—C(=O)—O—$CH_2$—$CH_2$—O—C(=O)—C($CH_3$)=$CH_2$<br>$CH_3$—$CH_2$/ |

I claim:
1. An amphiphilic monomer having a mixed-chain structure of the formula (I)

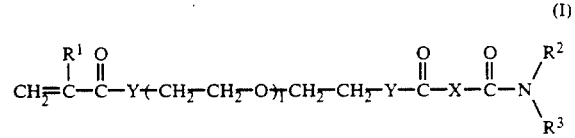

(I)

in which
Y denotes —O— or —NH—
X denotes a group of the formula —$(CH_2)_n$— or —$(CH_2$—O—$CH_2)_n$—
l denotes an integer from 0 to 10,
n denotes an integer from 1 to 10,
$R^1$ denotes hydrogen, methyl, chlorine, cyano, fluorine or bromine,
$R^2$ denotes $C_1$-$C_{24}$-alkyl or $C_1$-$C_{24}$-fluoroalkyl and $R^3$ denotes $C_8$–$C_{24}$-alkyl or $C_8$–$C_{24}$-fluoroalkyl, with the proviso that the groups $R^2$ and $R^3$ contain a different number of carbon atoms.

2. A polymer obtained by polymerization of one or more monomers of the formula (I) of claim 1.

3. A copolymer obtained by polymerization of one or more monomers of the formula (I) of claim 1 and one or more other, hydrophilic or hydrophobic comonomers.

4. The copolymer as claimed in claim 3 containing, as a result of polymerization, from 1 to 20% by weight of one or more monomers of said formula (I) and 99 to 80% by weight of at least one hydrophobic comonomer.

5. The copolymer as claimed in claim 3 containing, as a result of polymerization, from 10 to 99% by weight of one or more monomers of said formula (I) and 1 to 90% by weight of at least one hydrophilic comonomer.

6. A layer element with a solid layer support and a plurality of solid, thin, orderly arranged layers of a polymer as claimed in claim 2 applied to said support.

7. A layer element with a solid layer support and a plurality of solid, thin, orderly arranged layers of a polymer as claimed in claim 3 applied to said support.

8. A process for the preparation of a layer element as claimed in claim 6, which comprises dissolving at least one said polymer in a volatile organic water-immiscible solvent, spreading the solution on the water/air interface, compressing the resulting layer after evaporation of the solvent and transferring said layers to a solid layer support by the Langmuir-Blodgett technique.

9. A process for the preparation of a layer element as claimed in claim 7, which comprises dissolving at least one said polymer in a volatile organic water-immiscible solvent, spreading the solution on the water/air interface, compressing the resulting layer after evaporation of the solvent and transferring said layers to a solid layer support by the Langmuir-Blodgett technique.

* * * * *